(12) United States Patent
Oetjen et al.

(10) Patent No.: US 10,369,809 B2
(45) Date of Patent: Aug. 6, 2019

(54) METHOD AND APPARATUS FOR DIGITALLY PRINTING ABSORBENT ARTICLE COMPONENTS

(71) Applicant: The Procter & Gamble Company, Cincinnati, OH (US)

(72) Inventors: David C. Oetjen, West Chester, OH (US); Kasey M. Hudson, Cincinnati, OH (US); Horst Blessing, Cincinnati, OH (US)

(73) Assignee: Tue Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/719,625

(22) Filed: Sep. 29, 2017

(65) Prior Publication Data
US 2019/0100036 A1   Apr. 4, 2019

(51) Int. Cl.
*B41J 3/54* (2006.01)
*B41J 2/21* (2006.01)
*B41J 3/407* (2006.01)

(52) U.S. Cl.
CPC ............. *B41J 3/543* (2013.01); *B41J 2/2146* (2013.01); *B41J 3/407* (2013.01)

(58) Field of Classification Search
CPC ........... B41J 3/543; B41J 2/2146; B41J 3/407
See application file for complete search history.

(56) References Cited

U.S. PATENT DOCUMENTS

| | | | |
|---|---|---|---|
| 2,075,189 A | 10/1935 | Galligan et al. | |
| 3,025,199 A | 3/1962 | Harwood | |
| 3,465,350 A | 9/1969 | Keur et al. | |
| 3,465,351 A | 9/1969 | Keur et al. | |
| 3,848,594 A | 11/1974 | Buell | |
| 3,860,003 A | 1/1975 | Buell | |
| 4,107,364 A | 8/1978 | Sisson | |
| 4,209,563 A | 6/1980 | Sisson | |

(Continued)

FOREIGN PATENT DOCUMENTS

EP   1 528 907 B1   9/2008

OTHER PUBLICATIONS

PCT International Search Report, dated Dec. 14, 2018, 14 pages.

*Primary Examiner* — Lamson D Nguyen
(74) *Attorney, Agent, or Firm* — Andrew J. Hagerty; Sarah M. DeCristofaro

(57) ABSTRACT

The methods and apparatuses relate to digitally printing a substrate using first and second printheads. The first printhead includes a first printhead width and the second printhead includes a second printhead width. The first printhead overlaps with the second printhead such that the first printhead width overlaps with the second printhead width in a cross direction. The overlapping first and second printheads form a first print zone, an overlapping print zone, and a second print zone. The first printhead may deposit droplets onto the substrate in the first print zone and/or the overlapping zone. The second printhead may deposit droplets onto the substrate in the overlapping print zone and/or the second print zone. The droplets deposited in the overlapping print zone may unite to illustrate multiple colors and/or may remain ununited. By using overlapping printheads, various colors may be illustrated and the width of the substrate may be printed on.

5 Claims, 10 Drawing Sheets

(56) References Cited

U.S. PATENT DOCUMENTS

| | | |
|---|---|---|
| 4,321,924 A | 3/1982 | Ahr |
| 4,425,130 A | 1/1984 | DesMarais |
| 4,589,876 A | 5/1986 | Van Tilburg |
| 4,610,678 A | 9/1986 | Weisman et al. |
| 4,662,875 A | 5/1987 | Hirotsu et al. |
| 4,673,402 A | 6/1987 | Weisman et al. |
| 4,695,278 A | 9/1987 | Lawson |
| 4,704,115 A | 11/1987 | Buell |
| 4,795,454 A | 1/1989 | Dragoo |
| 4,834,735 A | 5/1989 | Alemany et al. |
| 4,834,741 A | 5/1989 | Sabee |
| 4,846,815 A | 7/1989 | Scripps |
| 4,888,231 A | 12/1989 | Angstadt |
| 4,894,060 A | 1/1990 | Nestegard |
| 4,909,803 A | 3/1990 | Aziz et al. |
| 4,940,464 A | 7/1990 | Van Gompel et al. |
| 4,946,527 A | 8/1990 | Battrell |
| 4,950,264 A | 8/1990 | Osborn, III |
| 5,092,861 A | 3/1992 | Nomura et al. |
| 5,151,092 A | 9/1992 | Buell et al. |
| 5,167,897 A | 12/1992 | Weber et al. |
| 5,221,274 A | 6/1993 | Buell et al. |
| 5,246,433 A | 9/1993 | Hasse et al. |
| 5,286,543 A | 2/1994 | Ungpiyakul et al. |
| 5,359,525 A | 10/1994 | Weyenberg |
| 5,360,420 A | 11/1994 | Cook et al. |
| 5,562,646 A | 10/1996 | Goldman et al. |
| 5,569,234 A | 10/1996 | Buell et al. |
| 5,581,284 A * | 12/1996 | Hermanson .......... B41J 2/04505 347/40 |
| 5,599,335 A | 2/1997 | Goldman et al. |
| 5,628,097 A | 5/1997 | Benson et al. |
| 5,643,588 A | 7/1997 | Roe et al. |
| 5,669,894 A | 9/1997 | Goldman et al. |
| 5,674,216 A | 10/1997 | Buell et al. |
| 5,702,551 A | 12/1997 | Huber et al. |
| 5,735,840 A | 4/1998 | Kline et al. |
| 5,916,661 A | 6/1999 | Benson et al. |
| 5,897,545 A | 7/1999 | Kline et al. |
| 5,928,212 A | 7/1999 | Kline et al. |
| 5,957,908 A | 9/1999 | Kline et al. |
| 5,968,025 A | 10/1999 | Roe et al. |
| 6,107,537 A | 8/2000 | Elder et al. |
| 6,107,539 A | 8/2000 | Palumbo et al. |
| 6,118,041 A | 9/2000 | Roe et al. |
| 6,120,487 A | 9/2000 | Ashton |
| 6,120,489 A | 9/2000 | Johnson et al. |
| 6,153,209 A | 11/2000 | Vega et al. |
| 6,251,097 B1 | 6/2001 | Kline et al. |
| 6,410,129 B2 | 6/2002 | Zhang et al. |
| 6,426,444 B2 | 7/2002 | Roe et al. |
| 6,432,098 B1 | 8/2002 | Kline et al. |
| 6,545,197 B1 | 4/2003 | Muller et al. |
| 6,586,652 B1 | 7/2003 | Roe et al. |
| 6,617,016 B2 | 9/2003 | Zhang et al. |
| 6,627,787 B1 | 9/2003 | Roe et al. |
| 6,669,618 B2 | 12/2003 | Reising et al. |
| 6,790,798 B1 | 9/2004 | Suzuki et al. |
| 6,801,828 B2 | 10/2004 | Popp et al. |
| 6,811,239 B1 | 11/2004 | Salacz |
| 6,820,022 B2 | 11/2004 | Popp et al. |
| 6,825,393 B2 | 11/2004 | Roe et al. |
| 6,861,571 B1 | 3/2005 | Roe et al. |
| 7,123,981 B2 | 10/2006 | Dollevoet et al. |
| 8,145,343 B2 | 3/2012 | DeBruler et al. |
| 8,145,344 B2 | 3/2012 | DeBruler et al. |
| 8,244,393 B2 | 8/2012 | McLaughlin et al. |
| 9,211,356 B2 | 12/2015 | Gruenbacher et al. |
| 9,434,155 B1 | 9/2016 | Linder et al. |
| 9,950,529 B2 * | 4/2018 | Koide ..................... B41J 2/51 |
| 2003/0090539 A1 * | 5/2003 | Lahut ................... B41J 2/2103 347/43 |
| 2003/0233082 A1 | 12/2003 | Kline et al. |
| 2004/0097895 A1 | 5/2004 | Busam et al. |
| 2004/0158212 A1 | 8/2004 | Ponomarenko et al. |
| 2007/0078427 A1 | 4/2007 | Raycheck et al. |
| 2007/0093769 A1 | 4/2007 | Kline et al. |
| 2009/0312730 A1 | 12/2009 | LaVon et al. |
| 2013/0072887 A1 | 3/2013 | LaVon et al. |
| 2013/0211356 A1 | 8/2013 | Nishikawa et al. |
| 2013/0306226 A1 | 11/2013 | Zink et al. |

* cited by examiner

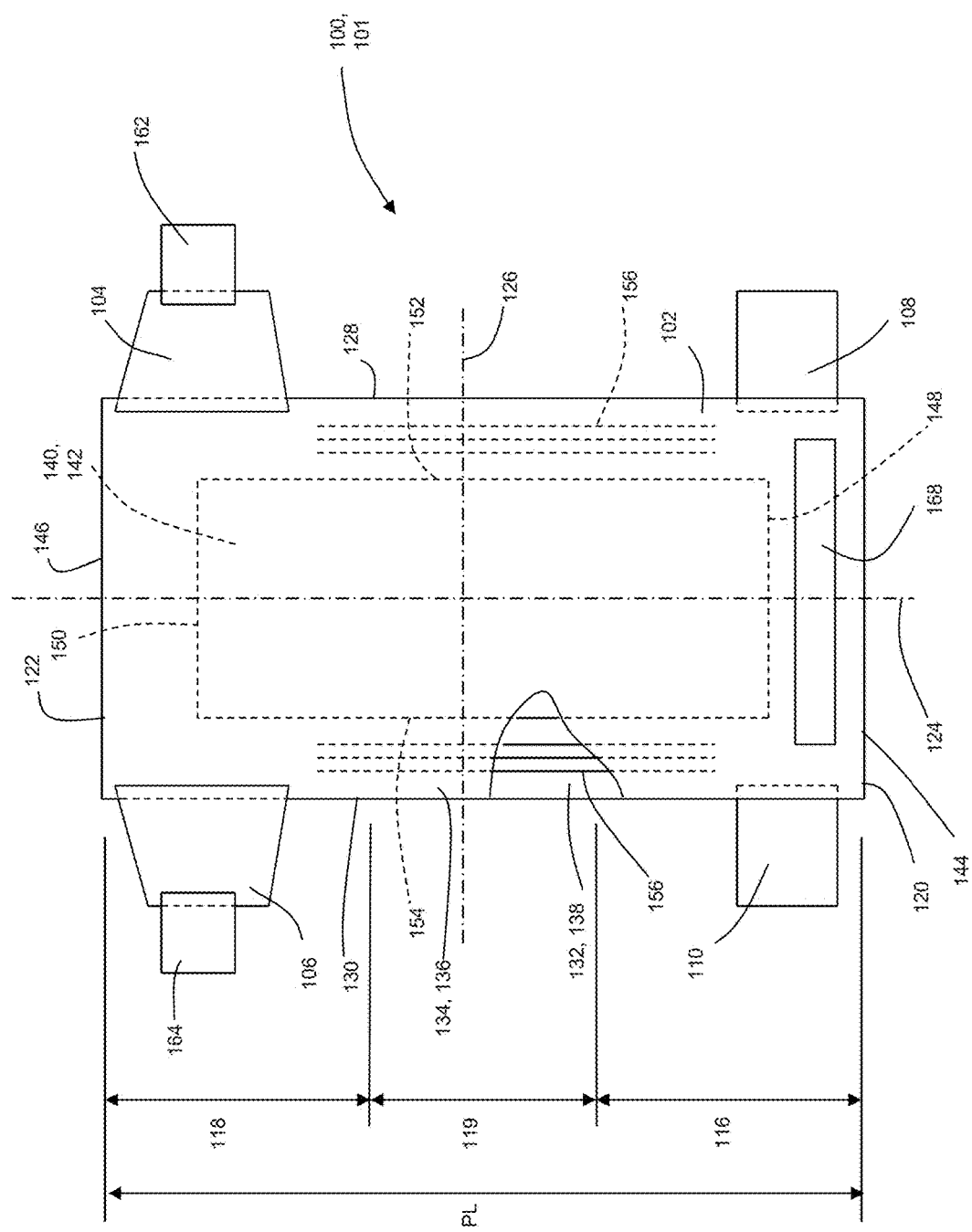

METHOD AND APPARATUS FOR DIGITALLY PRINTING ABSORBENT ARTICLE COMPONENTS

FIELD

The present disclosure relates to apparatuses and methods for digitally printing absorbent article component substrates advancing in a machine direction, and more particularly, methods and apparatuses with printheads arranged along the cross direction for printing regions of advancing substrates.

BACKGROUND

Along an assembly line, diapers, sanitary napkins, and various types of other disposable absorbent articles may be assembled by adding components to and otherwise modifying advancing, continuous webs of material. Webs of material and component parts used to manufacture diapers may include: backsheets, topsheets, absorbent cores, front and/or back ears, fastener components, and various types of elastic webs and components such as leg elastics, barrier leg cuff elastics, and waist elastics. Webs of material and component parts used to manufacture sanitary napkins may include: backsheets, topsheets, secondary topsheets, absorbent core components, release paper wrappers, and the like. In some configurations, graphics are printed on individual components and/or continuous webs of material used to assemble the absorbent articles. The graphics may be provided by printing ink on substrate materials by various printing methods, such as flexographic printing, rotogravure printing, screen-printing, inkjet printing, and the like.

In some configurations, the printing operations are performed separate to the assembly process, such as for example, printing the substrates offline wherein the printed substrates may be stored until needed for production. For example, printing operations may be accomplished on discrete printing lines, separately from converting lines that are dedicated to manufacturing disposable absorbent articles. After printing on the printing lines, the printed substrates are delivered to the converting lines, such as in a form of continuous webs comprising printed images thereon. However, the above practice of separately printing the substrates offline from the converting lines typically requires additional cost associated with handling, winding and unwinding, storing, and shipping of the substrates. In addition, the above steps can negatively affect the quality of the printed substrate, resulting in uneven and often excessive deformations of the wound layers of the substrate inside the roll due to uneven distribution of the compression forces inside the roll. Furthermore, the separately printed substrates often require special registration control methods to ensure proper phasing of the printed images with the converting operations to affect a desired and consistent positioning of the printed image in the produced article.

In an attempt to overcome the aforementioned drawbacks to offline printing, the graphic printing may be done online during the article assembly process. However, combining printing operations with converting operations may create other challenges in performing such printing processes when attempting to maintain aesthetically pleasing final assemblies. For example, contact printing processes, such as flexographic and rotogravure printing processes, may be capable of operating effectively on certain substrates at relatively high production rates. However, such contact printing processes have relatively low degrees of flexibility with regard to the ability to change the design of a printed graphic. When utilizing such contact printing methods, changes in graphic designs would often necessitate the shutdown and restart of the entire converting operation. In contrast, some types of printing processes, such as non-contact inkjet printing processes, may provide relatively high degrees of flexibility and ease with regard to the ability to change the design of a printed graphic. In some configurations, a change in graphic design can be implemented by simply inputting commands to a programmed printhead controller to select a desired image to be printed.

However, to obtain such graphics with multiple colors and relatively intricate designs, multiple printheads need to be used. These printheads extend in the cross direction to enable printing of the entire width of the substrate and also extend in the machine direction to enable printing with multiple colors and at desired resolutions. Generally, the more complex the design and the more colors of the graphic, the greater the number of printheads that need to be used. For example, when an area to be printed on a substrate is wider than the width of a single printhead, multiple printheads are stitched together, or stated another way, placed immediately adjacent to one another in the cross direction. This results in the printheads generally covering an area which extends beyond the area that needs to be printed and only a portion of the printhead is used for printing. Further, when the design requires more than one color, printheads are placed adjacent one another in the machine direction. Printheads of various colors may need to be used to color build, or stated another way, create a different color or the appearance of a different color using at least two other colors. For example, a graphic that requires the color purple would need to be printed with a printhead including cyan ink and a printhead including magenta ink. These printheads would be placed adjacent to one another in the machine direction. Generally the greater the number of colors a graphic requires the greater the number of printheads required. The printheads are relatively costly and often require backup printheads to ensure that production is not adversely impacted by a malfunctioning printhead.

Consequently, there remains a need to minimize the number of printheads while still maintaining the ability to produce products having multi-colored graphics and the ability to communicate product benefits to the consumer.

SUMMARY

The present disclosure relates to methods and apparatuses for digitally printing including printheads arranged along the cross direction in an overlapping configuration for printing regions of substrates at desired print resolutions and/or with various inks. In some embodiments, a method for digitally printing onto an advancing substrate may include: providing a first printhead, wherein the first printhead has a first printhead width extending in a cross direction; providing a second printhead, wherein the second printhead has a second printhead width extending in the cross direction, wherein a portion of the first printhead overlaps a portion of the second printhead in a cross direction to form a total printhead width; advancing a substrate in the machine direction past the first printhead and the second printhead, the substrate comprising a first surface, an opposing second surface, and a substrate width extending in the cross direction; depositing a first plurality of droplets on the first surface of the substrate using the first printhead; and depositing a second plurality of droplets on the first surface of the substrate using the second printhead.

In some embodiments, a method for digitally printing onto an advancing substrate may include: providing a first printhead, wherein the first printhead has a first printhead width extending in a cross direction; providing a second printhead, wherein the second printhead has a second printhead width extending in the cross direction, wherein a portion of the first printhead width overlaps a portion of the second printhead width in a cross direction to form a total printhead width and an overlapping print zone, wherein the first printhead defines a first print zone extending from the overlapping print zone in the cross direction to an edge of the first printhead, and wherein the second printhead defines a second print zone extending from the overlapping print zone in the cross direction to an edge of the second printhead; advancing a substrate in the machine direction past the first printhead and the second printhead, the substrate comprising a first surface, an opposing second surface, and a substrate width extending in the cross direction; depositing a first plurality of droplets on the first surface of the substrate using the first printhead, wherein the first plurality of droplets are deposited on at least a portion of the first print zone and a portion of the overlapping print zone; depositing a second plurality of droplets on the first surface of the substrate using the second printhead, wherein the second plurality of droplets are deposited on at least a portion of the second print zone and a portion of the overlapping print zone, wherein the first plurality of droplets comprise a first color and the second plurality of droplets comprise a second color, and wherein a portion of the first plurality of droplets unite with a portion of the second plurality of droplets in the overlapping print zone to form one or more combinations of colors.

In some embodiments, a method for digitally printing onto an advancing substrate may include: providing a first printhead, wherein the first printhead has a first printhead width extending in a cross direction; providing a second printhead, wherein the second printhead has a second printhead width extending in the cross direction, wherein a portion of the first printhead overlaps a portion of the second printhead in a cross direction to form a total printhead width and an overlapping print zone, wherein the first printhead defines a first print zone extending from the overlapping print zone in the cross direction to an edge of the first printhead, and wherein the second printhead defines a second print zone extending from the overlapping print zone in the cross direction to an edge of the second printhead; advancing a substrate in the machine direction past the first printhead and the second printhead, the substrate comprising a first surface, an opposing second surface, and a substrate width extending in the cross direction; depositing a first plurality of droplets on the first surface of the substrate using the first printhead, wherein the first plurality of droplets are deposited on at least one of a portion of the first print zone and a portion of the overlapping print zone; and depositing a second plurality of droplets on the first surface of the substrate using the second printhead, wherein the second plurality of droplets are deposited on at least one of a portion of the second print zone and a portion of the overlapping print zone.

BRIEF DESCRIPTION OF THE DRAWINGS

FIG. 1A is a partially cut away plan view of an absorbent article in the form of a taped diaper that may include one or more substrates printed in accordance with the present disclosure with the portion of the absorbent article that faces away from a wearer oriented towards the viewer.

DETAILED DESCRIPTION

Figure 1B:
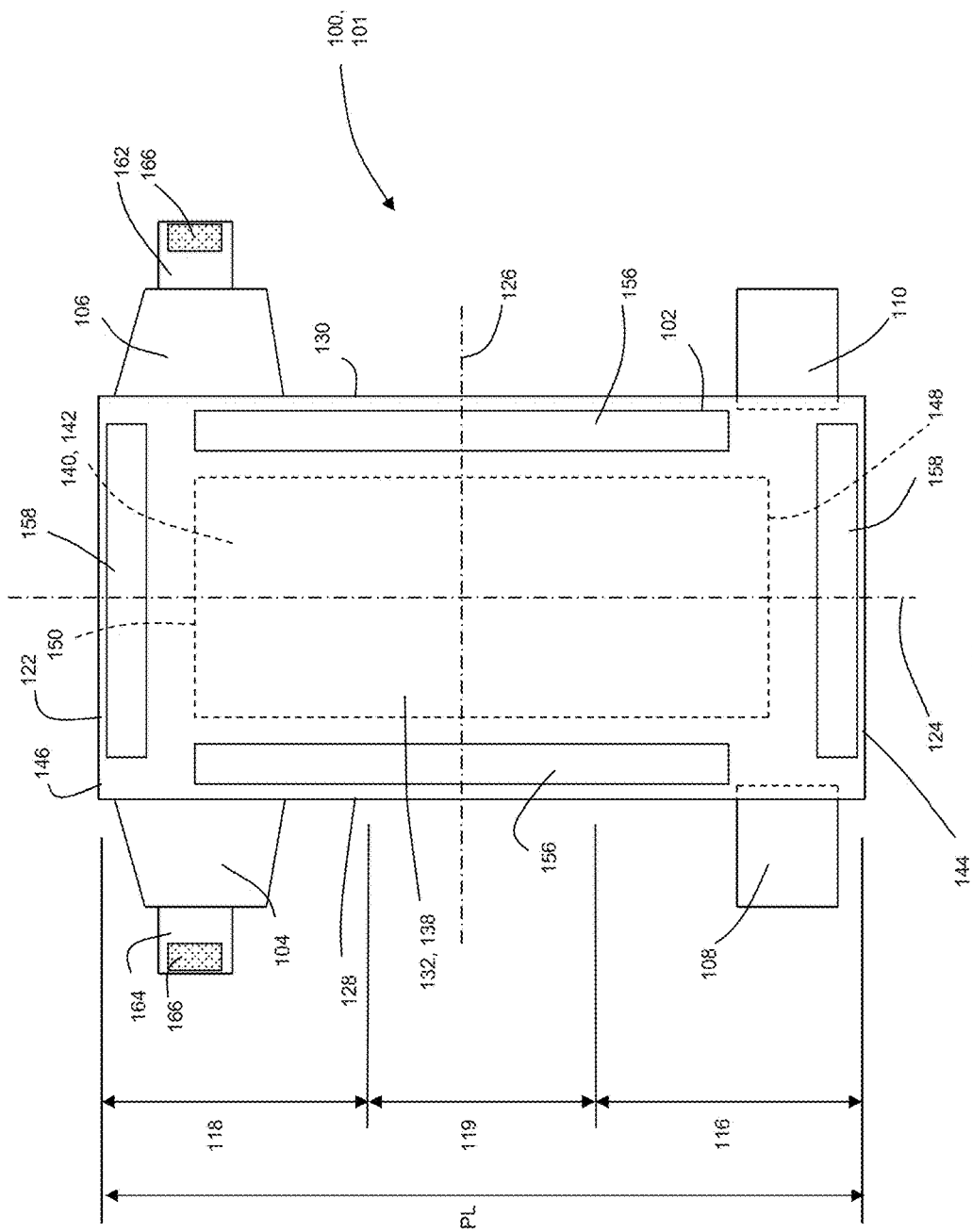
FIG. 1B is a plan view of the absorbent article of FIG. 1A that may include one or more substrates printed in accordance with the present disclosure with the portion of the absorbent article that faces toward a wearer oriented towards the viewer.

The following term explanations may be useful in understanding the present disclosure: "Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

The term "taped diaper" (also referred to as "open diaper") refers to disposable absorbent articles having an initial front waist region and an initial back waist region that are not fastened, pre-fastened, or connected to each other as packaged, prior to being applied to the wearer. A taped diaper may be folded about the lateral centerline with the interior of one waist region in surface to surface contact with the interior of the opposing waist region without fastening or joining the waist regions together. Example taped diapers are disclosed in various suitable configurations U.S. Pat. Nos. 5,167,897, 5,360,420, 5,599,335, 5,643,588, 5,674,216, 5,702,551, 5,968,025, 6,107,537, 6,118,041, 6,153,209, 6,410,129, 6,426,444, 6,586,652, 6,627,787, 6,617,016, 6,825,393, and 6,861,571; and U.S. Patent Publication Nos. 2013/0072887 A1; 2013/0211356 A1; and 2013/0306226 A1.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed or pre-fastened by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed). Example diaper pants in various configurations are disclosed in U.S. Pat. Nos. 5,246,433; 5,569,234; 6,120,487; 6,120,489; 4,940,464; 5,092,861; 5,897,545; 5,957,908; and U.S. Patent Publication No. 2003/0233082 A1.

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

As used herein, the term "graphic" refers to images or designs that are constituted by a figure (e.g., a line(s)), a symbol or character, a color difference or transition of colors, or the like. A graphic may include an aesthetic image or design that can provide certain benefit(s) when viewed. A graphic may be in the form of a photographic image. A graphic may also be in the form of a 1-dimensional (1-D) or 2-dimensional (2-D) bar code or a quick response (QR) bar code. A graphic design is determined by, for example, the color(s) used in the graphic (individual pure ink or spot colors as well as built process colors), the sizes of the entire graphic (or components of the graphic), the positions of the graphic (or components of the graphic), the movements of the graphic (or components of the graphic), the geometrical shapes of the graphic (or components of the graphics), the number of colors in the graphic, the variations of the color combinations in the graphic, the number of graphics printed, the disappearance of color(s) in the graphic, and the contents of text messages in the graphic.

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The present disclosure relates to methods and apparatuses for digitally printing, also referred to herein as inkjet printing, absorbent article substrates, and in particular, methods and apparatuses including printheads arranged along the cross direction for printing onto zones of advancing substrates. More specifically, the methods and apparatuses herein include at least a first printhead and a second printhead arranged in an overlapping configuration in the cross direction and configured to print zones of a substrate. The first printhead includes a first printhead width extending in the cross direction and the second printhead includes a second printhead width extending in the cross direction. A portion of the first printhead width overlaps a portion of the second printhead width in the cross direction to form an overlapping print zone and a total printhead width. The first printhead also defines a first print zone extending from the overlapping print zone in the cross direction to an edge of the first printhead and the second printhead defines a second print zone extending from the overlapping print zone in the cross direction to an edge of the second printhead. The overlapping print zone is positioned between the first print zone and the second print zone. The total printhead width, which is the width in the cross direction from the edge of the first printhead to the edge of the second printhead, may be adjusted such that the overlapping print zone covers an intended area of the substrate and/or to minimize or eliminate having the printhead extend beyond the edge of substrate and, thus, having unused portions of the printhead. As the substrate advances in the machine direction past the first printhead and the second printhead, the first printhead deposits droplets onto at least one of the first print zone and the overlapping print zone and the second printhead deposits droplets onto at least one of the second print zone and the overlapping print zone. The droplets deposited onto the overlapping print zone may unite to illustrate one or more colors or the droplets deposited by each of the first printhead and the second printhead may remain separate from one another. By overlapping the first printhead and the second printhead in the cross direction, various colors may be formed by the droplets of the first printhead and the second printhead in the overlapping print zone. Having the ability to use multiple colors allows manufactures to communicate properties of the product to the consumer. For example, the multiple colors in the overlapping print zone in combination with the colors of both the first print zone and the second print zone may allow benefits such as barrier protection, wing location, absorption, position (front and back), and the like to be communicated to the consumer upon using the product. Further, by using fewer printheads, while still having to ability to print multiple colors, results in a cost reduction to manufacturers. Further, by overlapping the first printhead and the second printhead, the overlapping print zone may include a graphic(s) having increased print resolution, relatively higher dpi, than graphics printed in the adjacent print zones. Having the ability to include print zones having various print resolutions also allows manufactures to communicate properties of the product to consumers, such as noted above.

Figure 2:
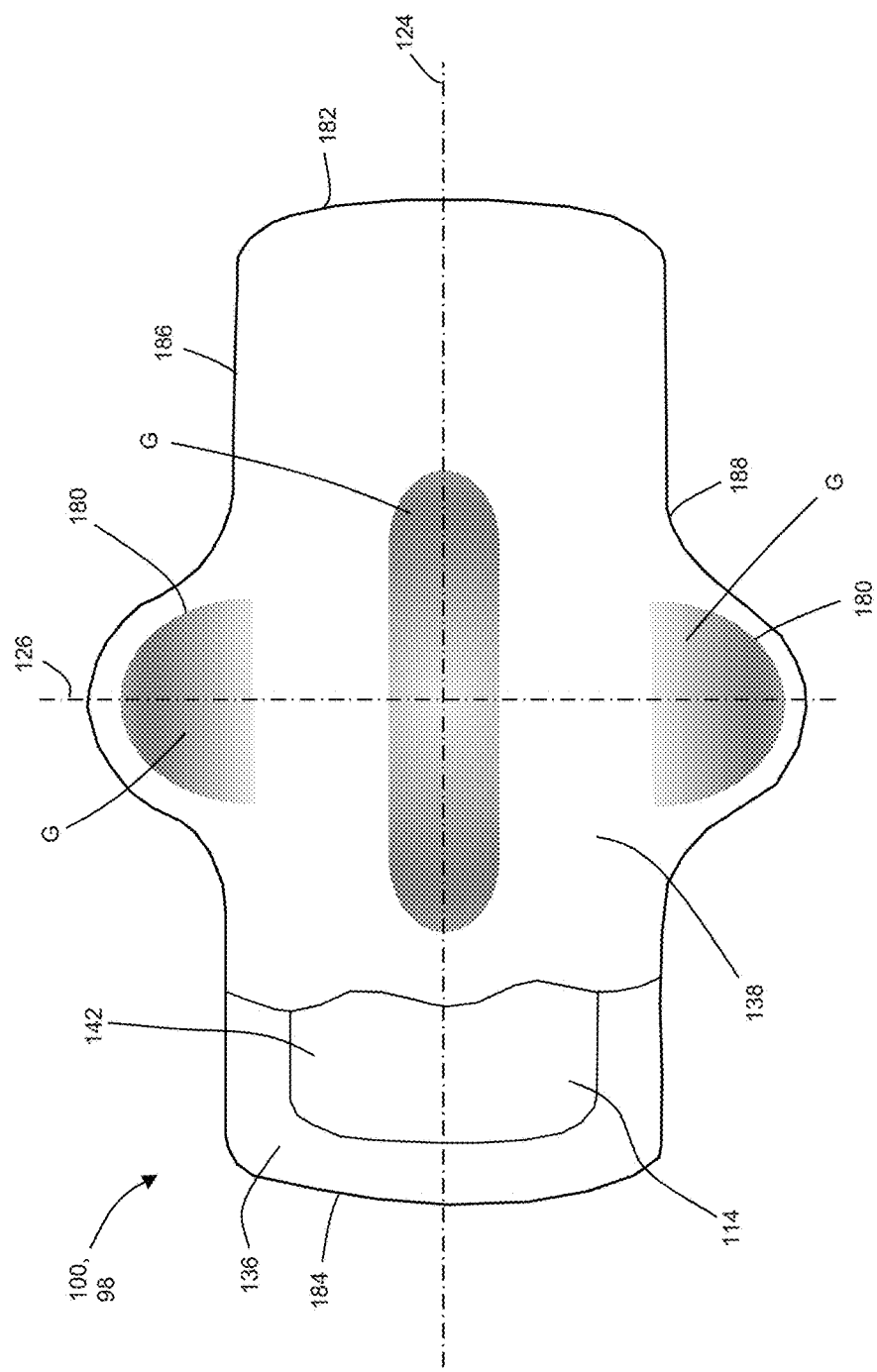
FIG. 2 is a plan view of the absorbent article that includes one or more substrates printed in accordance with the present disclosure.

It is to be appreciated that the apparatuses and methods disclosed herein are applicable to work with various types of converting processes and/or machines, such as for example, absorbent article manufacturing, packaging, and/or printing processes. The methods and apparatuses are discussed below in the context of manufacturing absorbent articles, such as diapers and sanitary napkins. And for the purposes of a specific illustration, FIGS. 1A, 1B, and 2 illustrate examples of absorbent articles 100 that may be printed in accordance with the methods and apparatuses disclosed herein. In particular, FIG. 1A shows one example of a plan view of an absorbent article 100 configured as a taped diaper 101, with the portion of the diaper that faces away from a wearer oriented towards the viewer. FIG. 1B shows a plan view of the diaper 101 with the portion of the diaper that faces toward a wearer oriented towards the viewer. FIG. 2 shows a plan view of a sanitary napkin 98.

The taped diaper 101 illustrated in FIGS. 1A and 1B includes a chassis 102, first and second rear side panels 104 and 106; and first and second front side panels 108 and 110. The diaper 101 and the chassis 102 each include a first waist region 116, a second waist region 118, and a crotch region 119 disposed intermediate the first and second waist regions. The first waist region 116 may be configured as a front waist region, and the second waist region 118 may be configured as back waist region. In some embodiments, the length of each of the front waist region, back waist region, and crotch region may be ⅓ of the length of the absorbent article 100. The absorbent article may also include a laterally extending front waist edge 120 in the front waist region 116 and a longitudinally opposing and laterally extending back waist edge 122 in the back waist region 118. To provide a frame of reference for the present discussion, the diaper 101 in FIGS. 1A and 1B is shown with a longitudinal axis 124 and a lateral axis 126. The longitudinal axis 124 may extend through a midpoint of the front waist edge 120 and through a midpoint of the back waist edge 122. And the lateral axis 126 may extend through a midpoint of a first longitudinal or right side edge 128 and through a midpoint of a second longitudinal or left side edge 130.

As illustrated in FIGS. 1A and 1B, the diaper 101 includes an inner, body facing surface 132, and an outer, garment facing surface 134. And the chassis 102 may include a backsheet 136 and a topsheet 138. The chassis 102 may also include an absorbent assembly 140, including an absorbent core 142, disposed between a portion of the topsheet 138 and the backsheet 136. As discussed in more detail below, the diaper 101 may also include other features, such as leg elastics and/or leg cuffs, an elastic waist region, and/or flaps, e.g., side panels and/or ears, to enhance the fits around the legs and waist of the wearer, to enhance the fit around the legs of the wearer.

The periphery of the chassis 102 may be defined by the first longitudinal side edge 128, a second longitudinal side edge 130, a first laterally extending end edge 144 disposed in the first waist region 116, and a second laterally extending end edge 146 disposed in the second waist region 118. Both side edges 128 and 130 extend longitudinally between the first end edge 144 and the second end edge 146. As shown in FIG. 1A, the laterally extending end edges 144 and 146 may form a portion of the laterally extending front waist edge 120 in the front waist region 116 and a portion of the longitudinally opposing and laterally extending back waist edge 122 in the back waist region 118. The distance between the first lateral end edge 144 and the second lateral end edge 146 may define a pitch length, PL, of the chassis 102. When the diaper 100 is worn on the lower torso of a wearer, the front waist edge 120 and the back waist edge 122 may encircle a portion of the waist of the wearer. At the same time, the side edges 128 and 130 may encircle at least a portion of the legs of the wearer. And the crotch region 119 may be generally positioned between the legs of the wearer with the absorbent core 142 extending from the front waist region 116 through the crotch region 119 to the back waist region 118.

It is to also be appreciated that a portion or the whole of the diaper 101 may also be made laterally extensible. The additional extensibility may help allow the diaper 101 to conform to the body of a wearer during movement by the wearer. The additional extensibility may also help, for example, the user of the diaper 101, including a chassis 102 having a particular size before extension, to extend the front waist region 116, the back waist region 118, or both waist regions of the diaper 101 and/or chassis 102 to provide additional body coverage for wearers of differing size, i.e., to tailor the diaper to an individual wearer. Such extension of the waist region or regions may give the absorbent article a generally hourglass shape, so long as the crotch region is extended to a relatively lesser degree than the waist region or regions, and may impart a tailored appearance to the article when it is worn.

As previously mentioned, the diaper 101 may include a backsheet 136. The backsheet 136 may also define the outer surface 134 of the chassis 102. The backsheet 136 may be impervious to fluids (e.g., menses, urine, and/or runny feces) and may be manufactured in part from a thin plastic film, although other flexible liquid impervious materials may also be used. The backsheet 136 may prevent the exudates absorbed and contained in the absorbent core from wetting articles which contact the diaper 101, such as bedsheets, pajamas and undergarments. The backsheet 136 may also comprise a woven or nonwoven material, polymeric films such as thermoplastic films of polyethylene or polypropylene, and/or a multi-layer or composite materials comprising a film and a nonwoven material (e.g., having an inner film layer and an outer nonwoven layer). The backsheet may also comprise an elastomeric film. An example backsheet 136 may be a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 136 may also be embossed and/or matte-finished to provide a more clothlike appearance. Further, the backsheet 136 may permit vapors to escape from the absorbent core (i.e., the backsheet is breathable) while still preventing exudates from passing through the backsheet 136. The size of the backsheet 136 may be dictated by the size of the absorbent core 142 and/or particular configuration or size of the diaper 101.

Also described above, the diaper 101 may include a topsheet 138. The topsheet 138 may also define all or part of the inner surface 132 of the chassis 102. The topsheet 138 may be compliant, soft feeling, and non-irritating to the wearer's skin. It may be elastically stretchable in one or two directions. Further, the topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art.

Topsheets 138 may be selected from high loft nonwoven topsheets, apertured film topsheets and apertured nonwoven topsheets. Apertured film topsheets may be pervious to bodily exudates, yet substantially non-absorbent, and have a reduced tendency to allow fluids to pass back through and rewet the wearer's skin. Exemplary apertured films may include those described in U.S. Pat. Nos. 5,628,097; 5,916,661; 6,545,197; and 6,107,539.

As mentioned above, the diaper 101 may also include an absorbent assembly 140 that is joined to the chassis 102. As illustrated in FIGS. 1A and 1B, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834,735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprise primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 A1 and 2004/0097895 A1.

As previously mentioned, the diaper 101 may also include elasticized leg cuffs 156 and an elasticized waistband 158. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695,278; 4,795,454; 4,704,115; and U.S. Patent Publication No. 2009/0312730 A1.

The elasticized waistband 158 may provide improved fit and containment and may be a portion or zone of the diaper 101 that may elastically expand and contract to dynamically fit a wearer's waist. The elasticized waistband 158 may extend longitudinally inwardly from the waist edges 120, 122 of the diaper toward the lateral edges 148, 150 of the absorbent core 142. The diaper 101 may also include more than one elasticized waistband 158, for example, having one waistband 158 positioned in the back waist region 118 and one waistband 158 positioned in the front wait region 116, although other embodiments may be constructed with a single elasticized waistband 158. The elasticized waistband 158 may be constructed in a number of different configurations including those described in U.S. Pat. Nos. 4,515,595 and 5,151,092. In some embodiments, the elasticized waistbands 158 may include materials that have been "pre-strained" or "mechanically prestrained" (subjected to some degree of localized pattern mechanical stretching to permanently elongate the material). The materials may be pre-strained using deep embossing techniques as are known in the art. In some embodiments, the materials may be pre-strained by directing the material through an incremental mechanical stretching system as described in U.S. Pat. No. 5,330,458. The materials are then allowed to return to their substantially untensioned condition, thus forming a zero strain stretch material that is extensible, at least up to the point of initial stretching. Examples of zero strain materials are disclosed in U.S. Pat. Nos. 2,075,189; 3,025,199; 4,107,364; 4,209,563; 4,834,741; and 5,151,092.

Taped diapers may be manufactured and provided to consumers in a configuration wherein the front waist region and the back waist region are not fastened, pre-fastened, or connected to each other as packaged, prior to being applied to the wearer. For example, the taped diaper 101 may be folded about a lateral centerline with the interior surface 132 of the first waist region 116 in surface to surface contact with the interior surface 132 of the second waist region 118 without fastening or joining the waist regions together. The rear side panels 104 and 106 and/or the front side panels 108 and 110 may also be folded laterally inward toward the inner surfaces 132 of the waist regions 116 and 118.

The diaper 101 may also include various configurations of fastening elements to enable fastening of the front waist region 116 and the back waist region 118 together to form a closed waist circumference and leg openings once the diaper is positioned on a wearer. For example, as illustrated in FIGS. 1A and 1B, the diaper 101 may include first and second fastening members 162, 164, also referred to as tabs, connected with the first and second rear side panels 104, 106, respectively. The diaper may also include first and second front side panels 108, 110, that may or may not include fastening members.

With continued reference to FIGS. 2A and 1B, each side panel 104, 106 and/or fastening member 162 and 164 may form a portion of or may be permanently bonded, adhered or otherwise joined directly or indirectly to the chassis 102 laterally inward from the side edge 128 and 130, in one of the front waist region 116 or the back waist region 118. Alternatively, the fastening members 162, 164 may form a portion of or may be permanently bonded, adhered or otherwise joined directly or indirectly to the first and second rear panels 104, 106 at or adjacent the distal edge of the panel and/or the first and second front side panels 108 and 110 at or adjacent the distal edge of the side panel. It is to be appreciated that the fastening members and/or side panels may be assembled in various ways, such as disclosed for example, in U.S. Pat. No. 7,371,302. The fastening members 162, 164 and/or side panels 104, 106, 108, 110 may also be permanently bonded or joined at or adjacent the side edges 128 and 130 of the chassis 102 in various ways, such as for example, by adhesive bonds, sonic bonds, pressure bonds, thermal bonds or combinations thereof, such as disclosed for example, U.S. Pat. No. 5,702,551.

Referring now to FIG. 1B, the first fastening member 162 and/or the second fastening member 164 may include various types of releasably engageable fasteners. The first and second fastening members 162 and/or 164 may also include various types of refastenable fastening structures. For example, the first and second fastening members 162 and 164 may include mechanical fasteners, 166, in the form of hook and loop fasteners, hook and hook fasteners, macrofasteners, buttons, snaps, tab and slot fasteners, tape fasteners, adhesive fasteners, cohesive fasteners, magnetic fasteners, hermaphroditic fasteners, and the like. Some examples of fastening systems and/or fastening members 162, 164 are discussed in U.S. Pat. Nos. 3,848,594; 4,662,875; 4,846,815; 4,894,060; 4,946,527; 5,151,092; 5,221,274; 6,251,097; 6,669,618; 6,432,098; and U.S. Patent Publication Nos. 2007/0078427 A1 and 2007/0093769 A1.

As previously mentioned, the fastening members 162 and 164 may be constructed from various materials and may be constructed as a laminate structure. The fastening members 162 and 164 may also be adapted to releasably and/or refastenably engage or connect with another portion of the diaper 101. For example, as shown in FIG. 1A, the diaper 101 may include a landing zone 168, in the first waist region 116. As such, when the taped diaper 101 is placed on a wearer, the fastening members 162 and 164 may be pulled around the waist of the wearer and connected within or at least partially within or adjacent to the landing zone 168 in the first waist region 116 to form a closed waist circumference and a pair of laterally opposing leg openings. It is to be appreciated that the landing zone may be constructed from a separate substrate that is connected with the chassis 102 of the taped diaper. In some embodiments, the landing zone may be integrally formed as part of the backsheet 136 of the diaper 101 or may be formed as part of the first and second front panels 108, 110, such as described in U.S. Pat. Nos. 5,735,840 and 5,928,212.

Figure 1C:
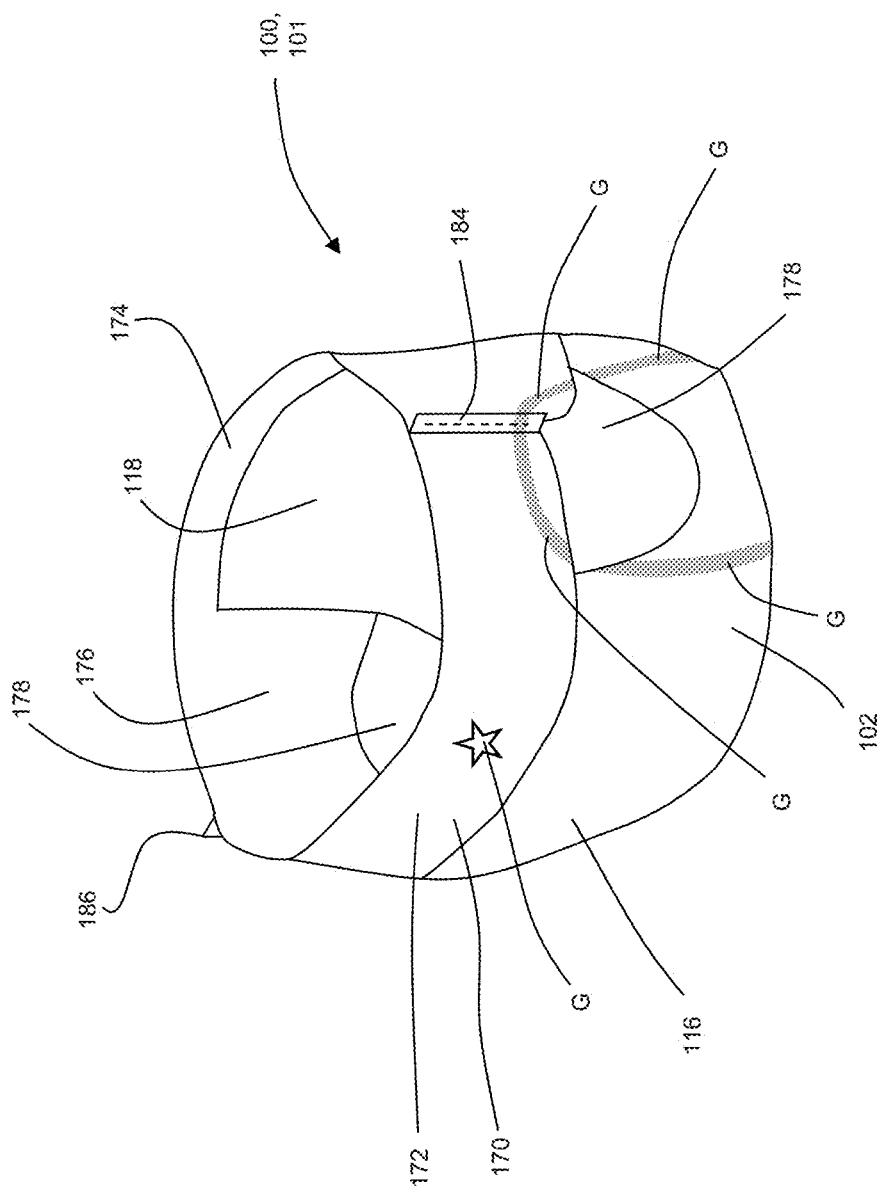
FIG. 1C is a front perspective view of an absorbent article in the form of a diaper pant with graphics on a chassis and front and rear belts.

As previously mentioned, absorbent articles 100 may also be configured as diaper pants 101 having a continuous perimeter waist opening and continuous perimeter leg openings. For example, FIG. 1C shows a perspective view of an absorbent article 100 in the form of a diaper pant 101 in a pre-fastened configuration. The diaper pant 101 may include a chassis 102 and a ring-like elastic belt 170 such as shown in FIG. 1C. In some embodiments, a first elastic belt 172 and a second elastic belt 174 are bonded together to form the ring-like elastic belt 170. As such, diaper pants may be manufactured with the ring-like elastic belt 174 and provided to consumers in a configuration wherein the front waist region 116 and the back waist region 118 of the chassis 102 are connected to each other as packaged, prior to being applied to the wearer. As such, diaper pants may have a continuous perimeter waist opening 176 and continuous perimeter leg openings 178.

As previously mentioned, the ring-like elastic belt 170 may be defined by a first elastic belt 172 connected with a second elastic belt 174. The first elastic belt is connected with the first waist region 116 of the chassis 102, and the second elastic belt 108 is connected with the second waist region 116 of the chassis 102. Opposing end regions of the first elastic belt 172 are connected with opposing end regions of the second elastic belt 174 at a first side seam 184 and a second side seam 186 to define the ring-like elastic belt 170 as well as the waist opening 176 and leg openings 178. It is to be appreciated that the ring-like elastic belt may be formed by joining a first elastic belt to a second elastic belt with permanent side seams or with openable and reclosable fastening systems disposed at or adjacent the laterally opposing sides of the belts.

FIG. 2 illustrates an example of an absorbent article 100 that may be printed in accordance with the methods and apparatuses disclosed herein. In particular, FIG. 2 illustrates one example of a plan view of an absorbent article 100 configured as a sanitary napkin 98. The sanitary napkin 98 may comprise a liquid permeable topsheet 138, a liquid impermeable, or substantially liquid impermeable, backsheet 136, and an absorbent core 142. The liquid impermeable backsheet 136 may or may not be vapor permeable. The absorbent core 142 may have any or all of the features previously described herein with respect to the absorbent core 142. In some embodiments, the sanitary napkin 98 may include a secondary topsheet 114 (STS) instead of or in addition to acquisition materials. The STS 114 may comprise one or more channels. Channels in the STS 114 may be aligned with channels in the absorbent core 142. The sanitary napkin 98 may also comprise wings 180 extending outwardly with respect to a longitudinal axis 124 of the sanitary napkin 98. The sanitary napkin 98 may also comprise a lateral axis 126. The wings 180 may be joined to the topsheet 138, the backsheet 136, and/or the absorbent core 142. The sanitary napkin 98 may also comprise a front edge 182, a back edge 184 longitudinally opposing the front edge 182, a first side edge 186, and a second side edge 188 longitudinally opposing the first side edge 186. The longitudinal axis 124 may extend from a midpoint of the front edge 182 to a midpoint of the back edge 184. The lateral axis 126 may extend from a midpoint of the first side edge 186 to a midpoint of the second side edge 188. The sanitary napkin 110 may also be provided with additional features commonly found in sanitary napkins as is known in the art.

With regard to the sanitary napkin 98 of FIG. 2, the secondary topsheet 114 incorporating fluid etched stratum of heterogeneous mass may be bonded to, or otherwise attached to the topsheet 138. In some embodiments, thermal point calendaring or other suitable bonding is utilized. In other embodiments, the fluid etched stratum of heterogeneous mass may serve as an absorbent core of an absorbent article. The fluid etched stratum of heterogeneous mass may serve as the topsheet for an absorbent article or the secondary topsheet of an absorbent article. Additionally, an absorbent article may utilize two or more fluid etched stratums of heterogeneous masses within one absorbent article. For example, panty liners and incontinence pads may be formed with the fluid etched stratum of heterogeneous mass positioned between a topsheet and a bottom sheet to function as an absorbent core. Furthermore, the fluid etched absorbent structure having a first layer and a second layer may not include a binder component.

The sanitary napkin 98 may have any shape known in the art for feminine hygiene articles, including the generally symmetric "hourglass" shape, as well as pear shapes, bicycle-seat shapes, trapezoidal shapes, wedge shapes or other shapes that have one end wider than the other.

The topsheet 138, the backsheet 136, and the absorbent core 142 may be assembled in a variety of well-known configurations, including so called "tube" products or side flap products, such as, for example, configurations are described generally in U.S. Pat. Nos. 4,950,264; 4,425,130; 4,321,924; and 4,589,876, all of which are incorporated by reference herein.

Figure 1D:
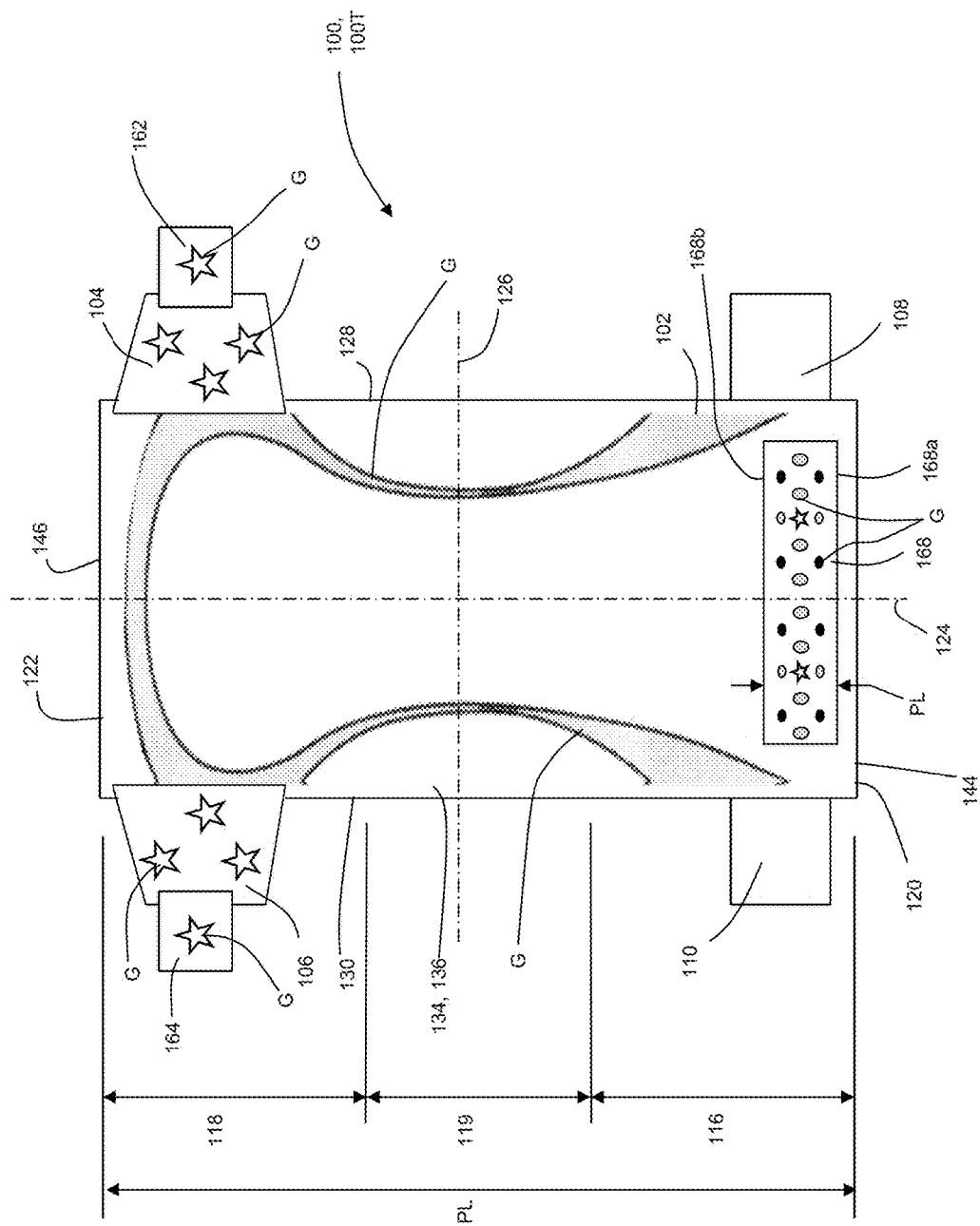
FIG. 1D is a plan view of an absorbent article that includes one or more substrates printed in accordance with the present disclosure with the portion of the absorbent article that faces away from a wearer oriented towards the viewer.

As previously mentioned, absorbent articles may be assembled with various components that may be printed off-line, before assembly, or on-line, as part of the assembly process. As such, the absorbent articles herein may include graphics printed on various components. Thus, in the context of the previous discussion, the apparatuses and methods herein may be used to print substrates configured as continuous substrates and/or discrete components of an absorbent article 100, either off-line or on-line. For example, the apparatuses and methods herein may be utilized to print graphics on any of the topsheet 138; backsheet 136; secondary topsheet 114; absorbent core 142; leg cuffs 156; waist feature 158; side panels 104, 106, 108, 110; fastening elements 162, 166, and/or belts before, during, and/or after the manufacture of an absorbent article 100. For example, the backsheet 136 of the taped diaper 101 shown in FIG. 1D includes graphics G that may be printed before, during, and/or after assembly. The various portions of the article shown in FIG. 1C may also include graphics G printed before, during, and/or after assembly. In yet another example, the front belt 172 and rear belt 174 of the diaper pant may include graphics G printed before, during, and/or after assembly. In yet another example, the secondary topsheet 114 of the sanitary napkin 98 shown in FIG. 2 includes graphics G that may be printed before, during, and/or after assembly. As discussed in more detail below, the systems and methods herein may be utilized to print such graphics before, during, and/or after assembly. Although the apparatuses and methods are described herein in the context of a feminine hygiene article, such as illustrated in FIG. 2, it is to be appreciated that the methods and apparatuses herein may be used to print various substrates that can be used with various process configurations and/or absorbent articles, such as for example, taped diapers and diaper pants, including adult incontinence articles.

Figure 3:
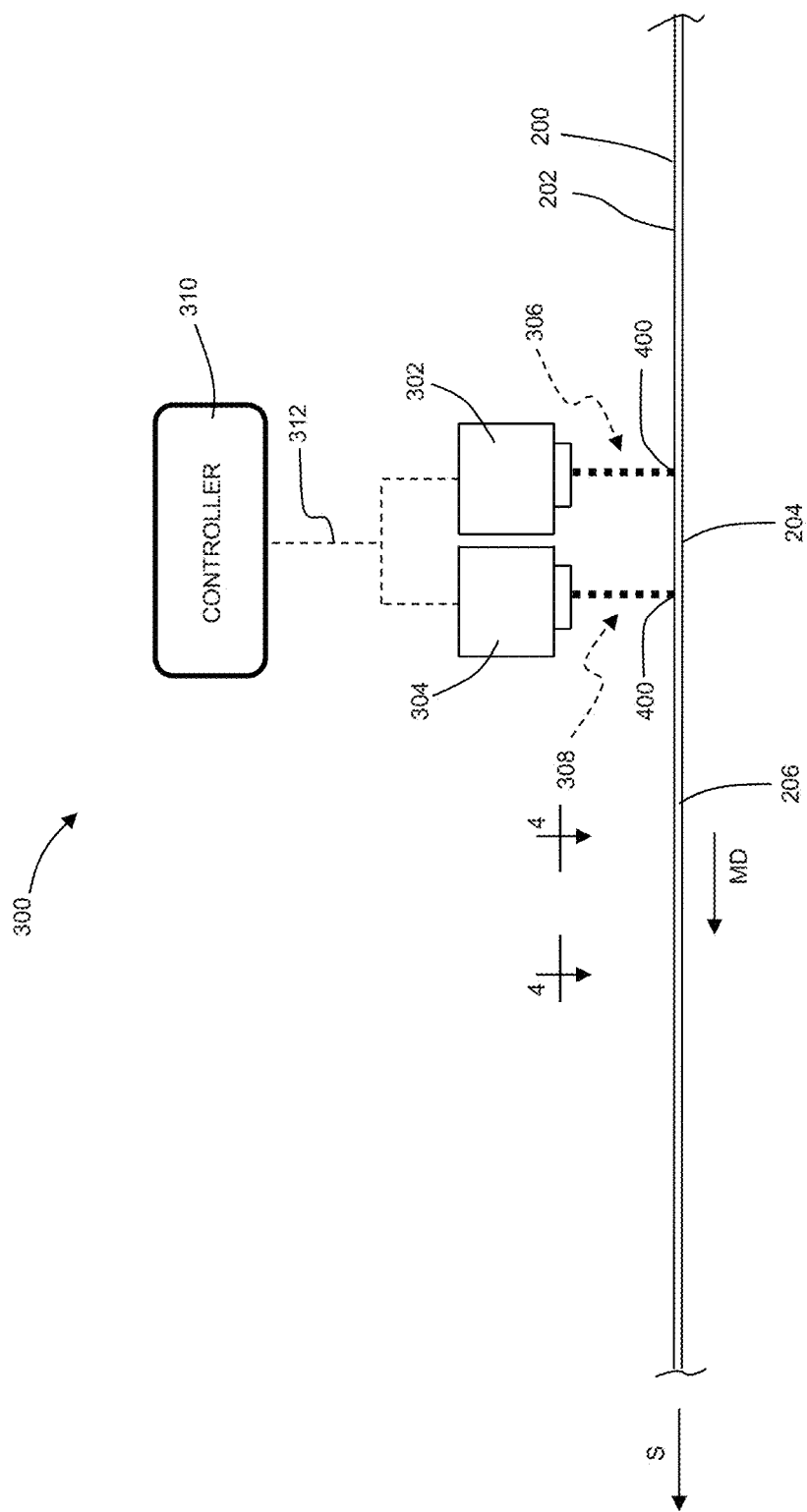
FIG. 3 is a schematic side view of a printing system for printing on an advancing substrate.
Figure 4:
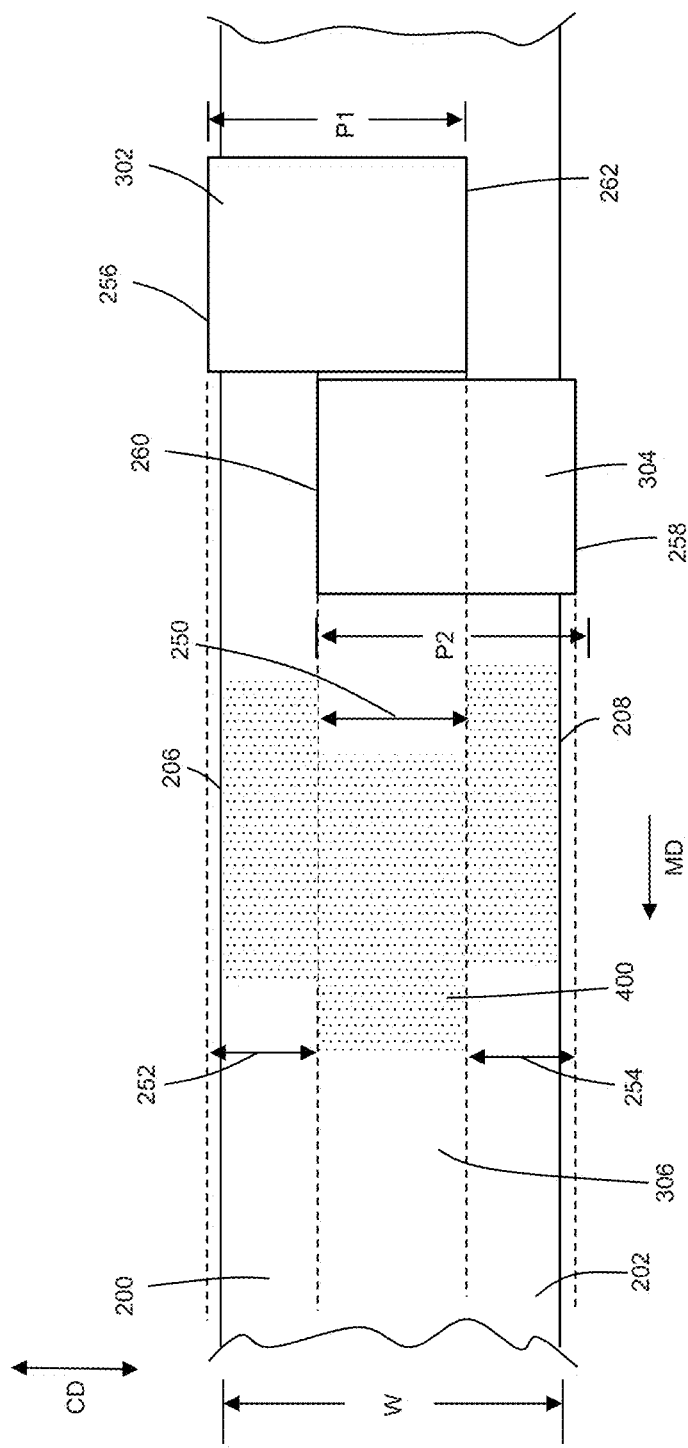
FIG. 4 is a top view of the advancing substrate taken along the sectional line 4-4 of FIG. 3.

It is to be appreciated that the printing systems and methods disclosed herein are applicable to work with various types of converting processes and/or machines. For example, FIG. 3 shows a schematic representation of a converting process including an inkjet apparatus or system 300 for printing graphics on a substrate 200 advancing in a machine direction MD. The substrate 200 may be a continuous substrate and may include a first surface 202 and an opposing second surface 204. The substrate 200 may also define a width W extending in the cross direction CD between a first longitudinal edge 206 and a second longitudinal edge 208, as illustrated in FIG. 4. It is to be appreciated that the substrate 200 may be subject to additional manufacturing operations, such as combining and/or cutting operations, during assembly of a product.

Referring to FIGS. 3 and 4, the printing system 300 may include a first printhead 302 and a second printhead 304. During operation, the substrate 200 advances in the machine direction MD under the first printhead 302 and the second printhead 304. The first printhead 302 has a first printhead width P1 extending in a direction substantially parallel to the cross direction CD and the second printhead has a second printhead width P2 extending in a direction substantially parallel to the cross direction CD. Each of the first printhead width P1 and the second printhead width P2 may be less than the width W of the substrate 200. The first printhead 302 and the second printhead 304 may be positioned with respect to one another such that the first printhead 302 is positioned adjacent to the second printhead 304 in the machine direction MD. The first printhead 302 may abut the second printhead 304 in the machine direction MD or there may be a gap in the machine direction MD between the first printhead 302 and the second printhead 304. The position of the printheads in the machine direction may be dependent upon available space in the assembly line, for example.

Further, to cover the width W of the substrate 200 in the cross direction CD, the first printhead 302 may be positioned over a portion of the substrate 200 and the second printhead 304 may be positioned over a portion of the substrate 200 such that, for example, the entire width W of the substrate 200 is covered by at least one of the first printhead 302 and the second printhead 304. More specifically, the first printhead 302 and the second printhead 304 may be positioned such that the first printhead width P1 overlaps with the second printhead width P2 forming an overlapping print zone 250, such as illustrated in FIG. 4. Generally, the greater the overlap between the first printhead 302 and the second printhead 304 the greater the width of the overlapping print zone 250. The outer edge 256 of the first printhead 302 may be adjacent to the first longitudinal edge 206 of the substrate 200. The outer edge 256 of the first printhead 302 may be positioned such that the outer edge 256 extends beyond the first longitudinal edge 206 in a direction perpendicular to the first longitudinal edge 206, such as illustrated in FIG. 4. The outer edge 256 of the first printhead 302 may also be planar with the first longitudinal edge 206 or the outer edge 256 of the first printhead 302 may be positioned between the first longitudinal edge 206 and the second longitudinal edge 208. The outer edge 258 of the second printhead 304 may be adjacent to the second longitudinal edge 208 of the substrate 200. The outer edge 258 of the second printhead 304 may be positioned such that the outer edge 258 extends beyond the second longitudinal edge 208 in a direction perpendicular to the second longitudinal edge 208, such as illustrated in FIG. 4. The outer edge 258 of the second printhead 304 may also be planar with the second longitudinal edge 208 or the outer edge 258 of the second printhead 304 may be positioned between the first longitudinal edge 206 and the second longitudinal edge 208. It is to be appreciated that the position of each printhead over the substrate should be such that the area intended to be printed on is covered by at least one of the first printhead and the second printhead.

Further, a first print zone 252 is formed by the outer edge 256 of the first printhead 302 adjacent the first longitudinal edge 206 of the substrate 200 and extending to the inner edge 260 of the second printhead or, stated another way, the edge of the overlapping print zone 250. Similarly, a second print zone 254 is formed by the outer edge 258 of the second printhead 304 adjacent the second longitudinal edge 208 of the substrate 200 and extending to the inner edge 262 of the first printhead or, stated another way, the edge of the overlapping print zone 250. It is to be appreciated that the first printhead 302 may print in any portion of or the entire width of the first print zone 252. Similarly, the second printhead 304 may print in any portion of or the entire width of the second print zone 254. The overlapping position of the first printhead 302 with the second printhead 304 allows multiple colors to be printed and for the entire width of the substrate to be printed on while limiting the number of total printheads. More specifically, the first printhead may deposit a plurality of droplets onto the first print zone and/or the overlapping zone and the second printhead may deposit a plurality of droplets onto the second print zone and/or the overlapping zone. The droplets deposited on the overlapping zone may unite to form, such as by illustration, various colors. Thus, the substrate may include multiple colors and all desired areas include color by using just two printheads.

Traditionally, to print multiple colors and to cover the entire width of an advancing substrate, a greater number of printheads would need to be used. For example, to print on the width of the substrate with multiple colors, such as with cyan and magenta, at least four printheads would be necessary. A first 500 and second 502 printhead including cyan ink would be placed adjacent one another in the cross direction such that the entire width of the substrate was covered.

Figure 5:
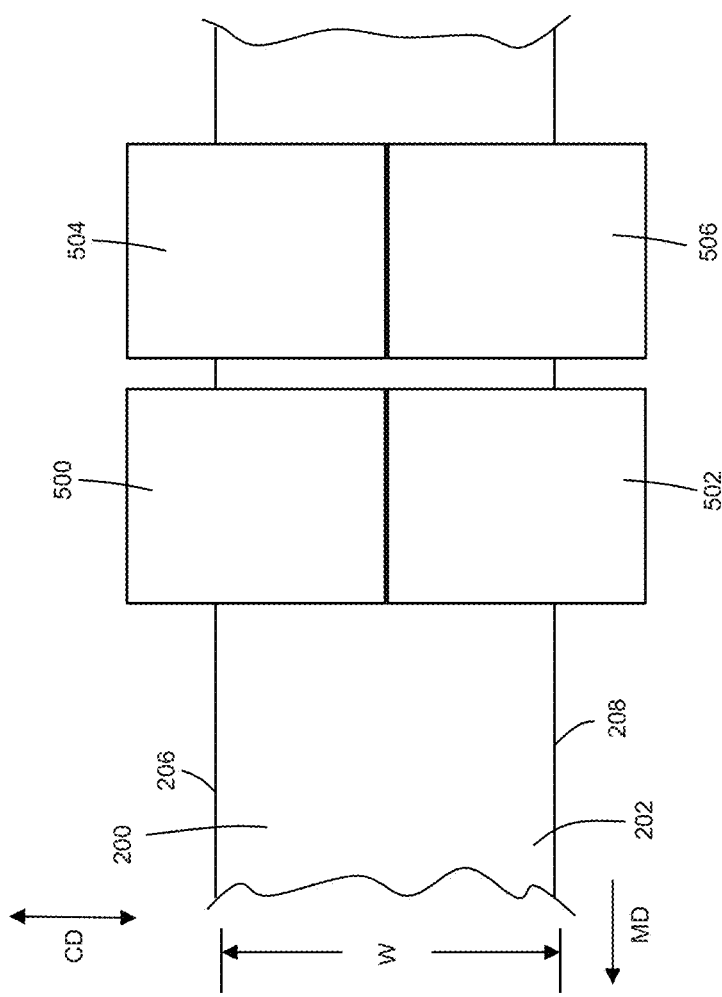
FIG. 5 is a top view of a printing system for printing on an advancing substrate.

Further, a third 504 and fourth 506 printhead including magenta ink would be positioned adjacent one another in the cross direction and on either side of the first 500 and second 504 printheads in the machine direction. Such a configuration is illustrated in FIG. 5. As illustrated in FIG. 5, the total width of the two printheads greatly exceeds the width of the substrate and four printheads are required to print the desired, multiple colors. Further, for each additional color required to be printed on the substrate, multiple additional printheads would be used.

By contrast, as illustrated in FIG. 4, two printheads are able to print the multiple colors without the addition of two extra printheads. It is to be understood that the second configuration, as illustrated in FIG. 4, may not allow certain colors to be printed in certain zone, but multiple colors may still be obtained with only two printheads. Further, having two printheads positioned in an overlapping configuration with one another allows the printheads to be used more efficiently. The printhead does not substantially overhang the edge of the substrate such that the whole printhead is not used for printing. Further still, by limiting the number of printheads while still having the capability to print multiple colors, manufacturers are able to save cost. Printheads are relatively expensive and manufacturers often keep backup printheads, at an additional cost, to keep the manufacturing line running in the event a problem occurs with the in-use printhead.

As illustrated in FIGS. 3 and 4, the first printhead 302 ejects a first ink 306 onto the first surface 202 of the advancing substrate 200. The first ink 306 may be deposited onto one or both of the first print zone 252 and the overlapping print zone 250. As the substrate 200 advances in the machine direction MD, the substrate is advanced under the second printhead 304. As shown in FIGS. 3 and 4, the second printhead 304 ejects a second ink 308 onto the first surface 202 of the advancing substrate 200. The second ink 308 may be deposited onto one or both of the second print zone 254 and the overlapping print zone 250. The ink need not cover the entire print zone. The ink may be selectively deposited onto the substrate to form, for example, a graphic which communicates some property of the absorbent article such as absorbency, structural characteristics (i.e., channels), and positioning for use (front and back).

Figure 6:
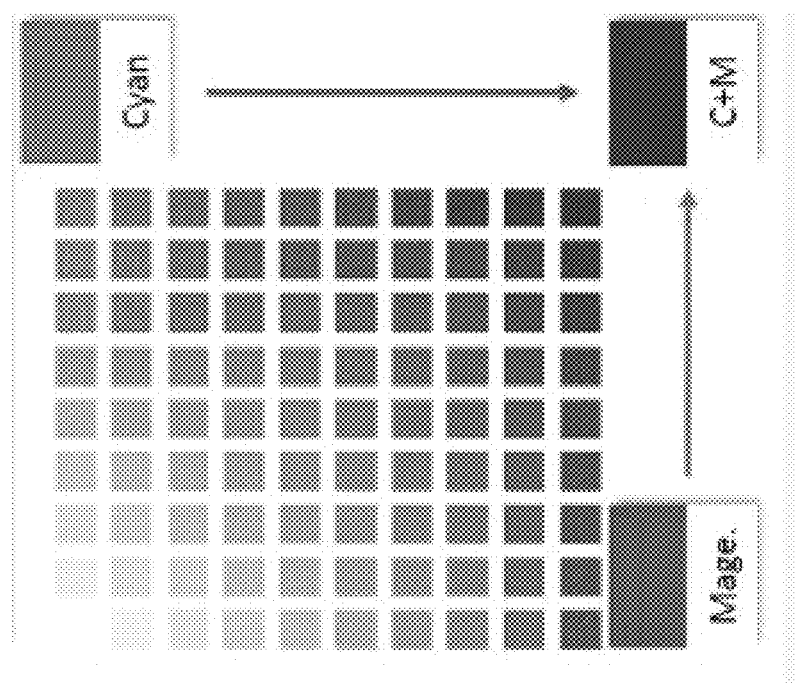
FIG. 6 is a chart of the color combinations using cyan ink and magenta ink for printing on an advancing substrate.

Further, as previously stated, the first ink 306 and the second ink 308 may both be deposited on the overlapping print zone 250. The first ink 306 may be deposited independent of the second ink 308 such that the color of each ink is not united. Additionally, the first ink 306 and the second ink 308 may be deposited on the overlapping print zone 250 such that the first ink 306 and the second ink 308 unite to illustrate a different color. It is to be appreciated that the overlapping print zone 250 may include areas where the first and second inks are not united and areas where the first and second inks are united. For example, the first ink 306 may have a cyan color and the second ink 308 may have a magenta color. In areas of the overlapping print zone 250 where the first ink and the second ink are ununited, the cyan color and the magenta color will be visible. In areas of the overlapping print zone 250 where the first ink and the second ink are united, some combination of the cyan color and the magenta color, such as purple, will be visible. FIG. 6 illustrates examples of the combination of colors that may be illustrated by combining cyan and magenta in the overlapping print zone 250.

It is to be appreciated that the printheads may deposit any color of droplets onto the substrate. For example, in some emboidments, the printheads may impart any one of cyan, magenta, yellow, or black.

It is to be appreciated that the advancing substrate 200 may be supported in various ways to mitigate movement toward and away from the printheads 302, 304. For example, the second surface 204 of the substrate 200 may be supported by a conveyor having a series of rollers, an advancing belt, and/or a rotating drum. In addition, first surface 202 may be positioned a certain distance away from the first printhead 302 and the second printhead 304. This distance may be adjusted to optimize printing. For example, the closer the printheads the greater control over the registration of graphics and/or color to color registration.

With reference to FIG. 3, it is to be appreciated that the printing apparatus 300 herein may include various quantities of non-contact printheads arranged and/or configured in various ways to deposit inks onto the advancing substrate 200 to create printed zones. For example, in some embodiments, the first and second printheads 302, 304 may be configured as inkjet printheads. Inkjet printing is a non-impact dot-matrix printing technology in which droplets of ink are jetted from a small orifice in the printhead directly to a specified position on a substrate to create a graphic. The inkjet printheads herein may be configured to perform different types of inkjet printing, such as for example, drop-on-demand, continuous, and thermal inkjet printing.

With "continuous" inkjet printing processes, in some embodiments, an ink is supplied under pressure to an inkjet nozzle and forced out through a small orifice. Prior to passing out of the nozzle, the pressurized ink stream proceeds through a ceramic crystal which is subjected to an electric current. The electric current causes a piezoelectric vibration equal to the frequency of an AC electric current. The vibration, in turn, generates the ink droplets from the unbroken ink stream. As such, the ink stream breaks up into a continuous series of drops which are equally spaced and of equal size. Surrounding the jet, at a point where the drops separate from the fluid stream in a charge electrode, a voltage is applied between the charge electrode and the drop stream. When the drops break off from the stream, each drop carries a charge proportional to the applied voltage at the instant at which it breaks off. By varying the charge electrode voltages at the same rate as drops are produced, it is possible to charge every drop to a predetermined level. The drop stream passes between two deflector plates which are maintained at a constant potential that deflects a drop towards one of the plates by an amount proportional to the charge carried. Drops that are uncharged are undeflected and collected into a gutter to be recycled to the ink nozzle. Those drops which are charged, and hence deflected, impinge on a substrate traveling at a high speed at right angles to the direction of drop deflection. By varying the charge on individual drops, a desired pattern can be printed.

Further, in some embodiments, a "continuous" inkjet printing process includes supplying an ink under pressure to an inkjet nozzle and forcing the ink out through a small orifice. The pressurized ink stream proceeds through an annular heater and the ink stream is subject to a heat pulse. The heat pulse creates individual ink drops. Depending on the timing and spacing of the heat pulse two different sizes of ink drops may be created. The smaller ink drops are deflected by a laminar air flow curtain to be recycled while the larger ink drops proceed through the air flow curtain to the print media, such as an advancing substrate.

With "drop-on-demand" inkjet printing processes, an ink is forced under pressure from the printhead through a relatively small orifice in the form of minute droplets by rapid pressure impulses. In some configurations, the orifice may have a diameter of about 0.0024 inches (5-50 microns). The rapid pressure impulses may be generated in the printhead by either expansion of a piezoelectric crystal vibrating at a high frequency or volatilization of a volatile composition (e.g. solvent, water, propellant) within the ink by rapid heating cycles. The piezoelectric crystal expansion causes the ink to pass through the orifice as minute droplets in proportion to the number of crystal vibrations. Thermal inkjet printers employ a heating element within the print head to volatilize a portion of the composition that propels the vast majority of fluid through the orifice nozzle to form droplets in proportion to the number of on-off cycles for the heating element. The ink is forced out of the nozzle when needed to print a spot on a substrate as part of a desired image. The minute droplets may also be energized to achieve an electrical charge and deflected as in the continuous inkjet printing process discussed above. Various inkjet printing processes are more particularly described in U.S. Pat. Nos. 3,465,350; 3,465,351; and 9,211,356.

As previously mentioned, the printing system 300 herein may be configured with various quantities and types of printheads that operate to deposit inks on an advancing substrate at various rates. For example, the first printhead 302 and the second printhead 304 shown in FIG. 3 may be configured as inkjet printheads. As such, when the first printhead 302 fires, a drop of first ink 306 is discharged from an orifice in the first printhead 302. And when the second printhead 304 fires, a drop of second ink 308 is discharged from an orifice in the second printhead 304. The rate at which drops of ink are discharged from an orifice in a printhead is referred to herein as "firing frequency" and may be expressed in units of kilohertz (kHz). In turn, the printheads herein may be configured to operate at various firing frequencies at or below a maximum firing frequency of the printhead. As such, it is to be appreciated that the printing system 300 herein may be configured with various quantities of printheads that may be configured to operate at the same or different firing frequencies. In addition, the printheads herein may be configured with the same or different maximum firing frequencies. For example, in some configurations, the printheads herein may be configured with maximum firing frequencies that are equal to or greater than 5 kHz, and may be configured with maximum firing frequencies of about 5 kHz to about 120 kHz and/or from about 300 kHz to about 450 kHz, specifically reciting all 0.1 kHz increments within the above-recited ranges and all ranges formed therein or thereby. In some embodiments, the printheads herein may be configured with maximum firing frequencies of about 400 kHz or about 450 kHz.

It is also to be appreciated that the printing system 300 herein may be configured to operate with various types of inks or ink systems, such as solvent-based, water-based, and ultraviolet (UV) cured inks. An "ink" is a liquid containing coloring matter, for imparting a particular hue to a substrate. An ink may include dyes, pigments, organic pigments, inorganic pigments, and/or combinations thereof. A non-limiting example of an ink would encompass spot colors. Additional non-limiting examples of inks include inks having white color. Additional non-limiting examples of inks include hot melt inks.

Some primary differences among the ink systems may relate to the method used for drying or curing the ink. For example, solvent-based and water-based inks are dried by evaporation, while UV cured inks are cured by chemical reactions. Inks may also include components, such as solvents, colorants, resins, additives, and (for ultraviolet inks only) UV-curing compounds, that are responsible for various functions. In some embodiments, a multi-stage printing system may be utilized. In some embodiments, to improve ink rub-off resistance, ink compositions used herein may contain a wax. Such waxes may include a polyethylene wax emulsion. Addition of a wax to the ink composition may enhance rub resistance by setting up a barrier which inhibits the physical disruption of the ink film after application of the ink to the fibrous sheet. Based on weight percent solids of the total ink composition, addition ranges for the wax may be from about 0.5% solids to 10% solids. An example polyethylene wax emulsion is JONWAX 26 supplied by S.C. Johnson & Sons, Inc. of Racine, Wis. Some embodiments may utilize inks such as Artistri® Inks available from DuPont™, including 500 Series Acid Dye Ink; 5000 Series Pigment Ink; 700 Series Acid Dye Ink; 700 Series Disperse Dye Ink; 700 Series Reactive Dye Ink; 700 Series Pigment Ink; 2500 Series Acid Dye Ink; 2500 Series Disperse Dye Ink; 2500 Series Reactive Dye Ink; 2500 Series Pigment Dye Ink; 3500 Series Disperse Dye Ink; 3500 Series Pigment Dye Ink; and Solar Brite™ Ink. Ink such as disclosed in U.S. Pat. No. 8,137,721 may also be utilized. Water-based inks that may be utilized are available from Environmental Inks and Coatings Corporation, Morganton, N.C., under the following code numbers: EH034677 (yellow); EH057960 (magenta); EH028676 (cyan); EH092391 (black); EH034676 (orange); and EH064447 (green). Some embodiments may utilized water based inks composed of food-grade ingredients and formulated to be printed directly onto ingestible food or drug products, such as Candymark Series inks available in colors such as black pro, red pro, blue pro, and yellow pro, available from Inkcups located in Danvers, Mass. Other broad ranges of general purpose and specialty inks may also be used, including food grade inks available from Videojet Technologies Inc. located in Wood Dale, Ill. Additional example inks include Collins 186-150-6 LED Cyan Ink; Collins 186-150-7 LED Magenta Ink; Collins 186-150-6 LED Yellow Ink; Collins 186-150-5 LED Black Ink; and Videojet Ink 99-51SR.

With continued reference to FIG. 3, it is to be appreciated that the printing apparatus 300 herein may be configured in various ways and may include various types of printing accessories. In some configurations, the printing apparatus 300 may include a corona treater, which may be positioned upstream of the printheads 302, 304. The corona treater may be configured to increase the surface energy of the surface of the substrate 200 to be printed. In some embodiments, the corona treater may be configured to increase the surface energy of the surface to be printed to about 42 dynes/cm. In some configurations, the printing apparatus 300 may print energy curable ink, such as ultraviolet or electron beam curable inks, and thus, may also include an ink curing apparatus. In some configurations, the ink curing apparatus may be in the form of an ultraviolet (UV) light source that may include one or more ultraviolet (UV) lamps, which may be positioned downstream of the printheads 302, 304 to help cure inks deposited onto the substrate 200. In some configurations, the ink curing apparatus may also include an infrared (IR) dryer light source that may include one or more infrared (IR) lamps, which may be positioned downstream of the printheads 302, 304 to help dry water-based or solvent-based inks deposited onto the substrate 200 to form the graphics. In some configurations, the ink curing apparatus may include an electron beam (EB or e-beam) generator that may include one or more e-beam electrodes, which may be positioned downstream of the printhead 302, 304 to help cure inks deposited onto the substrate 200.

As previously mentioned, the printing system 300 may be configured to print off-line or interact with and/or be configured as a unit operation of a converting line. In some configurations of the printing system 300, the printheads 302, 304 may be arranged adjacent the advancing substrate 200, and the printheads 302, 304 may interface and communicate with a controller 310. The controller 310 may be adapted to control the operation of the printheads and/or allow an operator to manually program the type of graphics to be printed. For example, the printing system 300 may be configured with various features, such as available on the XD070 Multi-Color Industrial Ink Jet unit available from Pad Print Machinery of Vermont. In some configurations, the printing system 300 may be configured to interface with other computerized systems and/or networks that may automatically program or command the printing system to print various graphics based on various input, such as sales orders from customers. It is to be appreciated that the controller 310 may be configured in various ways. For example, the controller 310 may be in the form of a personal computer (PC) or a central processing unit (CPU). The controller 310 may also be configured to monitor and affect various operations on a converting line. For example, the controller 310 may send various types of control commands to the converting line based on communications with sensors adjacent the converting line.

It is to be appreciated that the controller 310 may also be configured to communicate with one or more computer systems, such as for example, a programmable logic controller (PLC) and/or personal computer (PC) running software and adapted to communicate on an EthernetIP network. Some embodiments may utilize industrial programmable controllers such as the Siemens S7 series, Rockwell ControlLogix, SLC or PLC 5 series, or Mitsubishi Q series. The aforementioned embodiments may use a personal computer or server running a control algorithm such as Rockwell SoftLogix or National Instruments Labview or may be any other device capable of receiving inputs from sensors, performing calculations based on such inputs and generating control actions through servomotor controls, electrical actuators or electro-pneumatic, electrohydraulic, and other actuators. In some configurations, process and product data may be stored directly in the aforementioned computer systems or may be located in a separate data historian. In some embodiments, the historian is a simple data table in the controller. In other embodiments, the historian may be a relational or simple database. Common historian applications include Rockwell Automation Factory Talk Historian, General Electric Proficy Historian, OSI PI, or any custom historian that may be configured from Oracle, SQL or any of a number of database applications. It is also to be appreciated that the controller 310 may be configured to communicate with various types of controllers and inspection sensors configured in various ways and with various algorithms to provide various types of data and perform various functions, for example, such as disclosed in U.S. Pat. Nos. 5,286,543; 5,359,525; 6,801,828; 6,820,022; 7,123,981; 8,145,343; 8,145,344; and 8,244,393; and European Patent No. EP 1528907 B1, all of which are incorporated by reference herein.

As shown in FIG. 3, the printheads 302, 304 may be in communication with the controller 310 through a communication network 312. As such, it is to be appreciated that the controller 310 may be physically located near the advancing substrate 200 and/or printheads 302, 304 and/or may be located at another location and in communication with the printheads 302, 304 via a wired and/or wireless network 312. In some embodiments, the communication network 312 is configured as a non-deterministic communication network, such as for example, Ethernet or Ethernet IP (industrial protocol) communication network.

As discussed above, the printing system 300 herein is configured to print on the substrate 200 at a desired print resolution. The term "print resolution" as used herein is defined in terms of inkjet printing technology by Dots Per Inch (dpi), wherein dpi defines a density of dots of ink that can be printed across a one inch length of a substrate. It is to be appreciated the printheads herein may be configured to print at various print resolutions in the cross direction CD and the machine direction MD.

The CD print resolution of a printed zone printed by a particular printhead may be affected in part by aspects of the printhead design, such as the number of orifices arranged in the cross direction CD. For example, in some configurations, the printheads herein may be configured to print zones at cross direction CD print resolutions of from about 80 dpi to about 128 dpi and/or from about 300 dpi to about 1200 dpi, specifically reciting all 1 dpi increments within the above-recited ranges and all ranges formed therein or thereby. In some configurations, the CD print resolution may be equal to about 600 dpi.

The MD print resolution of a printed zone printed by a particular printhead on a substrate may be affected by the firing frequency of the printhead and the speed at which the substrate advances in the machine direction MD. At a particular machine direction MD advancement speed of a substrate, the machine direction MD print resolution of a printed zone provided by a printhead may be increased and decreased by increasing and decreasing, respectively, the firing frequency of the printhead. Conversely, at a particular firing frequency, the machine direction MD print resolution of a printed zone provided by a printhead may be increased and decreased by decreasing and increasing, respectively, the machine direction MD advancement speed of the substrate. Thus, the MD print resolution may be directly proportional to a firing frequency of a printhead up to the maximum firing frequency of the printhead, whereas the MD print resolution may be inversely proportional to MD advancement speed of the substrate.

In some configurations, the substrates 200 herein may be advanced in the machine direction MD at various speeds, and as such, the printheads may be configured to print the advancing substrate with printed regions having various machine direction MD print resolutions. For example, the substrate 200 may be configured to advance in the machine direction MD at a first speed of about 0.5 meters/second (m/s) to about 15 m/s and/or from about 5 m/s to about 10 m/s, specifically reciting all 1 m/s increments within the above-recited ranges and all ranges formed therein or thereby. In some configurations, the first speed is equal to or greater than about 5 m/s. In turn, the printheads herein may be configured to print zones having machine direction MD print resolutions of about 10 dpi to about 6000 dpi, specifically reciting all 1 dpi increments within the above-recited ranges and all ranges formed therein or thereby. In some configurations, the MD print resolution may be equal to or greater than about 300 dpi.

Figure 7:
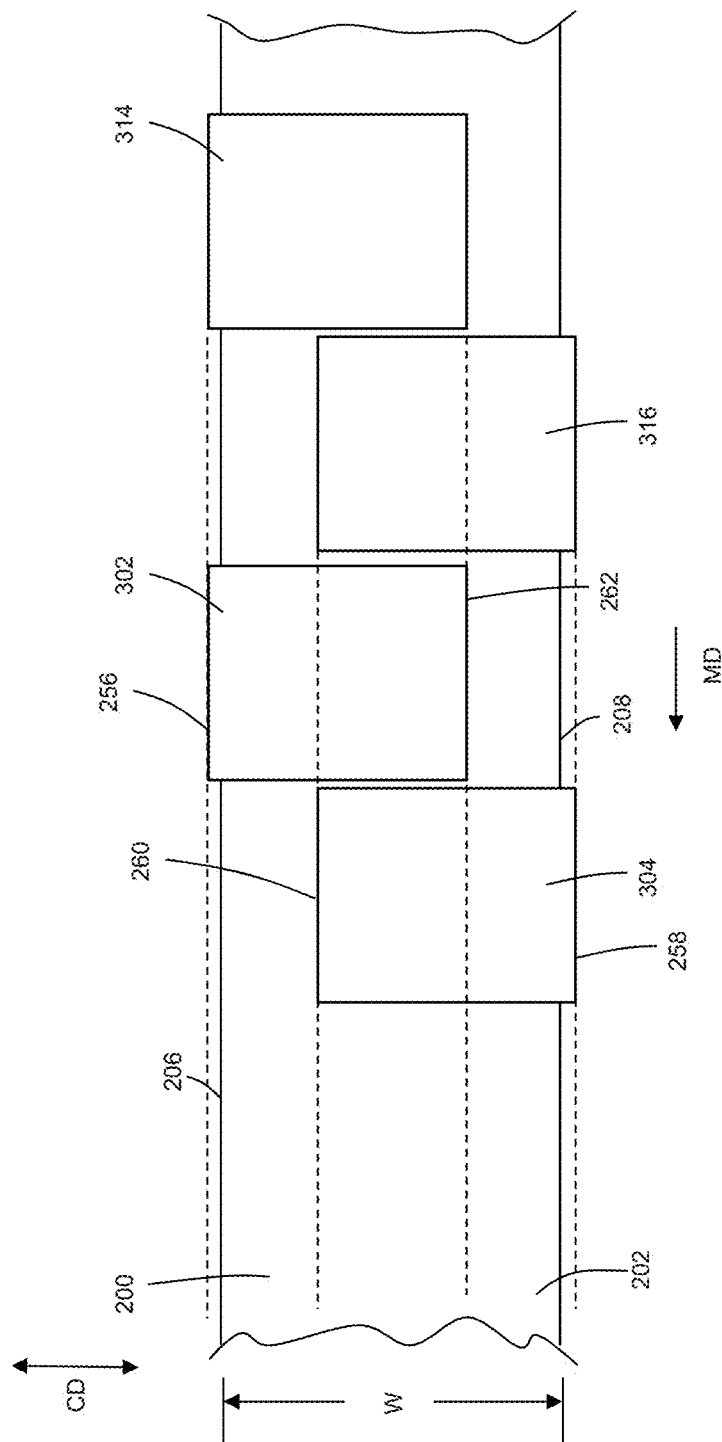
FIG. 7 is a top view of a printing system for printing on an advancing substrate.

As mentioned above, if a printhead operates at a maximum firing frequency to print a printed zone on a substrate, the MD print resolution of the printed zone will decrease as the substrate speed is increased. Thus, with prior art inkjet printing systems, if a desired MD print resolution is greater than the MD print resolution which can be achieved by a printhead operating at the maximum firing frequency, then the MD advancement speed of the substrate will have to be decreased to achieve the desired print resolution. However, the printing system 300 herein may overcome the aforementioned shortcoming by utilizing additional printheads positioned adjacent the printheads previously disclosed, such as illustrated in FIG. 7. A third printhead 314 and a fourth printhead 316 positioned in a configuration such as previously described works together with the first printhead 302 and the second printhead 306 to print having a desired MD print resolution that is greater than print resolutions achievable by either printhead operating alone at respective maximum firing frequencies while printing the substrate 200 advancing in the machine direction MD. It is to be appreciated that the any of the printheads may operate at various firing frequencies. For example, the firing frequency of the first printhead may be the same as or different than the firing frequency of the second printhead. It is also to be appreciated that any number of printheads may be added in the machine direction MD.

It is to be appreciated that the printing systems 300 herein may be configured to print in print zones at desired print resolutions on a substrate 200, wherein the printed droplets may form graphics G, such as discussed above with reference to absorbent articles assembled with various components that may be printed off-line, before assembly, or on-line, as part of the assembly process. Thus, in the context of the previous discussion, the printing system 300 herein may be used to print substrates and components of an absorbent article 100, either off-line or on-line. For example, the printing system 300 herein may be utilized to print printed regions to form graphics on any of the topsheet 138; backsheet 136; absorbent core 140; leg cuffs 156; waist feature 158; side panels 104, 106, 108, 110; connection zones 168; fastening elements 162, 166, and/or belts before or during the manufacture of an absorbent article 100.

Although the above discussion often refers to figures illustrating a printing system having a first printhead and a second printhead, it is to be appreciated that the printing systems herein may be configured with more than two or more printheads arranged in the cross direction CD and/or machine direction MD. In some configurations, the print system 300 herein may include backup printheads, such as disclosed in U.S. Pat. No. 6,811,239. It is also to be appreciated that the first ink 306 and the second ink 308 may be the same colors or may be different colors. For example, the first ink 306 may comprise a first color, and the second ink 308 may comprises a second color different from the first color. In another example, the first ink 306 may comprises a first color, and the second ink may comprise a second color that is the same as the first color. In addition, the printheads herein may be configured to perform single color, multicolor, half tone, and process printing.

"Halftone" or "halftoning" as used herein, sometimes referred to as "screening," is a printing technique that allows for less-than-full saturation of the primary colors. In halftoning, relatively small dots of each primary color are printed in a pattern small enough such that the average human observer perceives a single color. For example, magenta printed with a 20% halftone will appear to the average observer as the color pink. The reason for this is because, without wishing to be limited by theory, the average observer may perceive the tiny magenta dots and white paper between the dots as lighter, and less saturated, than the color of pure magenta ink. A "base color," as used herein, refers to a color that is used in the halftoning printing process as the foundation for creating additional colors. In some non-limiting embodiments, a base color is provided by a colored ink. Non-limiting examples of base colors may be selected from the group consisting of: cyan, magenta, yellow, black, red, green, and blue-violet. "Black", as used herein, refers to a color and/or base color which absorbs wavelengths in the entire spectral region of from about 380 nm to about 740 nm. "Cyan", as used herein, refers to a color and/or base color which have a local maximum reflectance in the spectral region of from about 390 nm to about 570 nm. In some embodiments, the local maximum reflectance is between the local maximum reflectance of the blue or blue-violet and green local maxima. "Magenta", as used herein, refers to a color and/or base color which have a local maximum reflectance in the spectral region of from about 390 nm to about 490 nm and 621 nm to about 740 nm. "Yellow", as used herein, refers to a color and/or base color which have a local maximum reflectance in the spectral region of from about 571 nm to about 620 nm.

"Process Printing," as used herein, refers to the method of providing color prints using at least three of the primary of colors cyan, magenta, yellow, and black. Other colors such as red, green, blue (RGB) or any orthogonal color may be used to expand the color gamut. Each layer of color is added over a base substrate. In some embodiments, the base substrate is white or off-white in color. With the addition of each layer of color, certain amounts of light are absorbed (those of skill in the printing arts will understand that the inks actually "subtract" from the brightness of the white background), resulting in various colors. CMY (cyan, magenta, yellow) are used in combination to provide additional colors. Non-limiting examples of such colors are red, green, and blue. K (black) is used to provide alternate shades and pigments. One of skill in the art will appreciate that CMY may alternatively be used in combination to provide a black-type color.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for digitally printing onto an advancing substrate, the method comprising:

providing a first printhead, wherein the first printhead has a first printhead width extending in a cross direction;

providing a second printhead, wherein the second printhead has a second printhead width extending in the cross direction, wherein a portion of the first printhead overlaps a portion of the second printhead in a cross direction to form a total printhead width and an overlapping print zone, wherein the first printhead defines a first print zone extending from the overlapping print zone in the cross direction to an edge of the first printhead, and wherein the second printhead defines a second print zone extending from the overlapping print zone in the cross direction to an edge of the second printhead;

advancing a substrate in the machine direction past the first printhead and the second printhead, the substrate comprising a first surface, an opposing second surface, and a substrate width extending in the cross direction;

depositing a first plurality of droplets on the first surface of the substrate using the first printhead, wherein the first plurality of droplets are deposited on at least one of a portion of the first print zone and a portion of the overlapping print zone;

depositing a second plurality of droplets on the first surface of the substrate using the second printhead, wherein the second plurality of droplets are deposited on at least one of a portion of the second print zone and a portion of the overlapping print zone; and adjusting at least one of the first printhead and the second printhead in the cross direction to form a second overlapping zone, wherein the second overlapping print zone has a different width than the overlapping print zone.

2. The method of claim 1, wherein the total printhead width is about equal to the substrate width.

3. The method of claim 1, comprising adjusting at least one of the first printhead and the second printhead in the cross direction such that the total printhead width is about equal to the greatest substrate width.

4. The method of claim 1, wherein the first plurality of droplet comprise a first color and the second plurality of droplets comprise a second color.

5. The method of claim 4, wherein the first color is different than the second color.

* * * * *